(12) United States Patent
El-Sabawi

(10) Patent No.: US 8,123,689 B1
(45) Date of Patent: Feb. 28, 2012

(54) DEVICE FOR LOCATING AND MARKING CONTACT POINT BETWEEN SKIN OF A PATIENT AND CENTER OF ULTRASOUND TRANSDUCER

(76) Inventor: Rashad El-Sabawi, Las Vegas, NV (US)

( * ) Notice: Subject to any disclaimer, the term of this patent is extended or adjusted under 35 U.S.C. 154(b) by 958 days.

(21) Appl. No.: 12/121,022

(22) Filed: May 15, 2008

(51) Int. Cl.
*A61B 8/00* (2006.01)
(52) U.S. Cl. ........................................................ 600/437
(58) Field of Classification Search .................. 600/407, 600/437
See application file for complete search history.

(56) References Cited

U.S. PATENT DOCUMENTS

| | | | | |
|---|---|---|---|---|
| 5,058,501 A | * | 10/1991 | Skopek | 101/334 |
| 5,755,746 A | * | 5/1998 | Lifshey et al. | 607/50 |
| 7,223,238 B2 | * | 5/2007 | Swanbom | 600/437 |

* cited by examiner

*Primary Examiner* — Jacqueline Cheng
(74) *Attorney, Agent, or Firm* — Greenberg Traurig

(57) ABSTRACT

A device for finding and marking the point of contact between the center of an ultrasound probe with skin of a patient and method of use thereof is disclosed. The device includes a block member having a handle. The block member includes a protrusion capable of making an indentation on skin of a subject. A ring member defining an aperture is configured to guide the block member into contact with skin of a subject such that the protrusion forms an indentation on a patient's skin. The indentation serves to mark the location which may then be used to identify an injection site (e.g., epidural) or other medical treatment procedure location. The injection or treatment location is found using a transducer or ultrasound for which the ring member is adapted to receive in advance of the block member.

14 Claims, 3 Drawing Sheets

DEVICE FOR LOCATING AND MARKING CONTACT POINT BETWEEN SKIN OF A PATIENT AND CENTER OF ULTRASOUND TRANSDUCER

FIELD OF THE INVENTION

The embodiments of the present invention relate to medical devices, more specifically, to a device for finding and marking the point of contact between the center of an ultrasound probe with skin of a patient and method of use thereof.

BACKGROUND

Ultrasound or ultrasonography is a medical imaging technique that uses sound waves and their echoes for a vast number of applications including monitoring fetuses, detecting intra-abdominal abnormalities and physical therapy, to name a few. During an ultrasound exam, a transducer probe capable of sending and receiving sound waves is directly applied to skin closest to the target area to obtain the required images. In some instances, it may be desirous to precisely know the point on the skin where the probe detected the desired image. The center of the probe is the point from which the beam of ultrasound is propagated and marking where the center of the probe touches the skin would be helpful in many applications mainly epidural and spinal needle placements As such, there exists a need for a device for finding where the center of a transducer probe contacts the skin and method of use thereof.

SUMMARY

Accordingly, a first embodiment of the present invention discloses a device comprising: a block member having a handle, said block member including means capable of making an indentation on skin of a subject; and a ring member defining an aperture, said aperture configured to guide said block member into contact with skin of a subject. In one embodiment, the aperture is also defined configured to accept an transducer or ultrasound probe.

A method embodiment of the present comprises: inserting a transducer probe into an aperture defined by said ring member such that said transducer probe is able to contact skin of a patient during use in conjunction with said ring member; pressing said transducer probe into contact with skin of a patient to locate a desired area on the patient; upon locating said desired area, pressing said ring member into contact with the skin of the patient near the desired area; removing said transducer probe from said ring member while retaining said ring member in contact with skin of a patient near said desired area; and inserting a marking member into said aperture defined by said ring member such that a marking protrusion on a block member of said marking member contacts skin of a patient and creates an indentation corresponding to said desired area.

In one embodiment of the present invention, the handle is elongated and takes on a circular cross-section. The block member, handle and ring member can be fabricated of wood, metal, plastic or other suitable material. The device and methods described herein may be used on humans or animals.

Other variations, embodiments and features of the present invention will become evident from the following detailed description, drawings and claims.

DETAILED DESCRIPTION

It will be appreciated by those of ordinary skill in the art that the invention can be embodied in other specific forms without departing from the spirit or essential character thereof. The presently disclosed embodiments are therefore considered in all respects to be illustrative and not restrictive.

Figure 1:
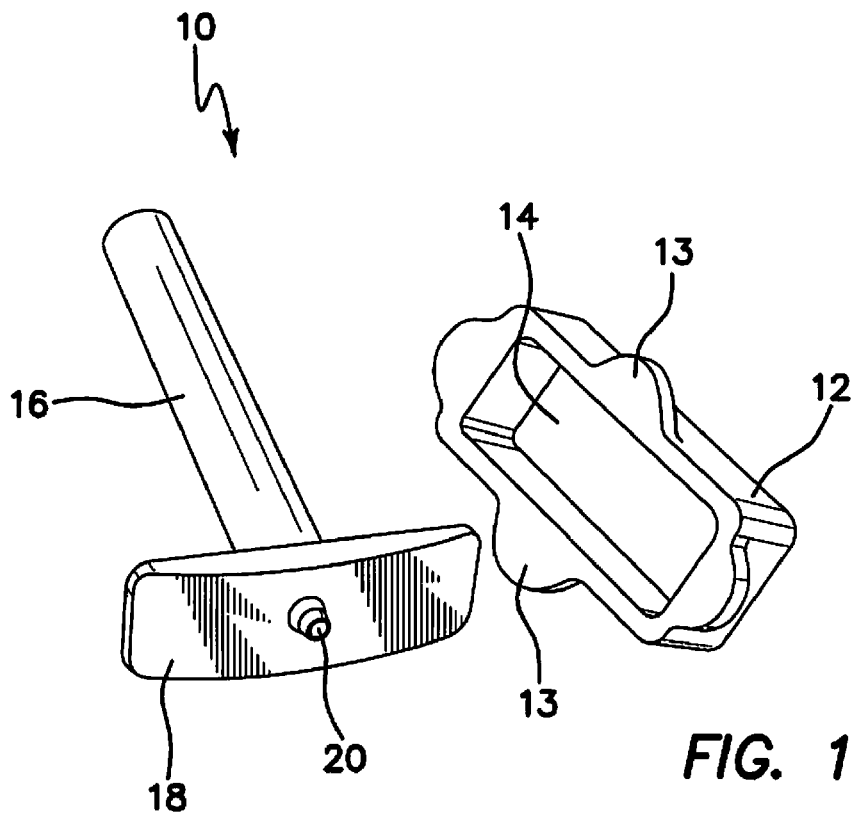
FIG. 1 illustrates a perspective view of a device for locating the center of an ultrasound transducer probe according to a first embodiment of the present invention.

Initial reference is made to FIG. 1 illustrating a perspective view of a device 10 for locating the center of an ultrasound transducer probe (not shown) according to a first embodiment of the present invention. The device 10 includes a rectangular ring member 12 having an aperture 14 defined thereby. Those skilled in the art will recognize that the ring member 14 may take on other shapes. Grips 13 extending from each wall of the ring member 14 provide means for handing the ring member 14 for reasons detailed below. The ring member 12 may be fabricated of wood, metal, plastic or other suitable material and can be formed using molding or other techniques. A marking member 15 includes a block member 18 positioned near one end of an elongated handle 16 having a circular cross-section. The aperture 14 is configured to receive and guide the block member 18 for reasons detailed below. The block member 18 is shown having a non-planar configuration. Those skilled in the art will recognize that the block member 18 and handle 16 may take on different shapes and configurations. Like the ring member 12, the handle 16 and block member 18 may be fabricated of wood, metal, plastic or other suitable material.

A marking protrusion 20 extends from a surface of the block member 18. In one embodiment, the marking protrusion 20 is circular in cross-section and culminates in a dull point. The size and sharpness of the point may vary depending on the desired accuracy level of the mark to be created. Moreover, the marking protrusion 20 may take on various lengths and cross-sections. The marking protrusion 20 may also take on other shapes and sizes as necessary so long as it is capable of making an indentation when pressed against a patient's skin. As shown, the marking protrusion 20 is positioned at the center of the block member 18. In an alternative embodiment, the marking protrusion 20 is configured to discharge ink, marking agent or any composition capable of marking a patient's skin.

Figure 2:
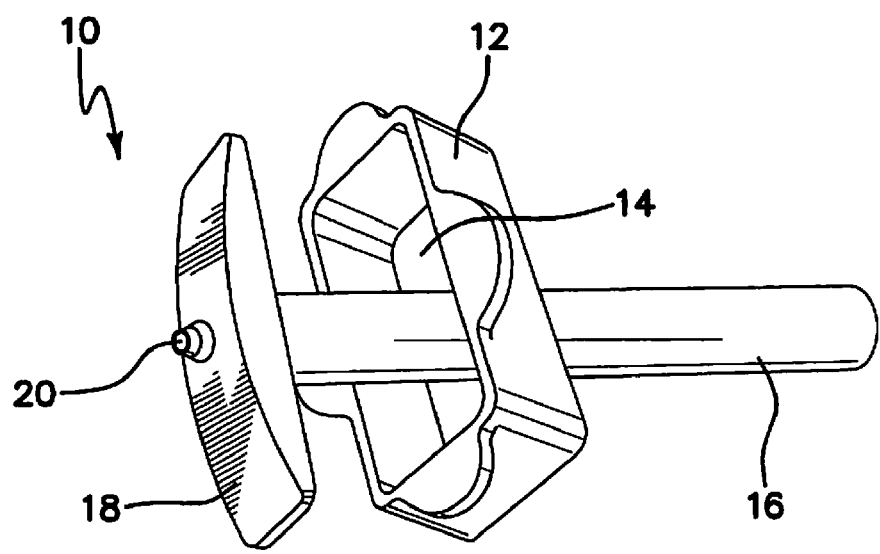
FIG. 2 illustrates a perspective view of the device of FIG. 1 demonstrating the coupling between two members of the device.

Reference is now made to FIG. 2 illustrating a perspective view of the device 10 demonstrating the interaction between the ring member 12 and the block member 18. In operation, a user holds the handle 16 and introduces the block member 18 into and through the aperture 14 of the ring member 12. The dimension of the aperture 14 is such that the block member 18 is not able to move with much freedom while surrounded by walls forming the ring member 14. In other words, the dimensions of the aperture 14 and block member 18 are substantially the same or within close tolerances. Once received by the aperture 14, movement of the block member 18 can be synchronized with that of the ring member 12 such that the two members 12, 18 move in unison. In other instances, the ring member 12 is used to guide and receive the block member 18 to facilitate making an indentation on the surface of a patient skin with the marking protrusion 20.

Figure 3:
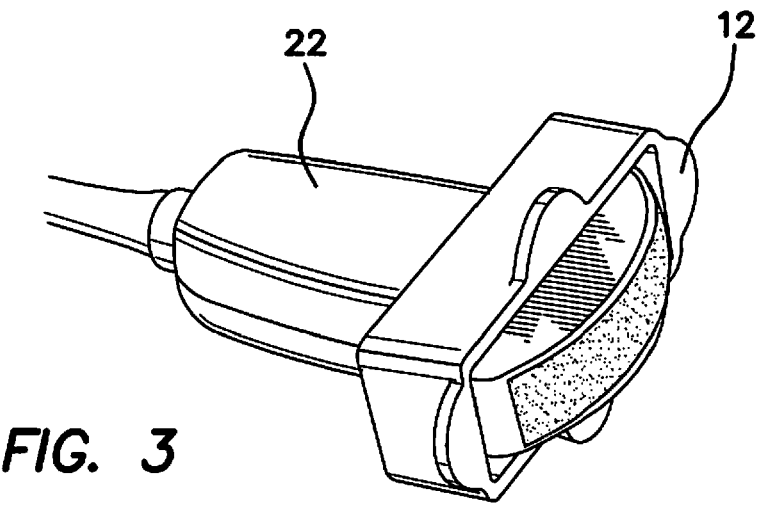
FIG. 3 illustrates a perspective view of a transducer probe being received by a ring member of the device.

Reference is now made to FIG. 3 illustrating a transducer or ultrasound probe 22 inserted into the aperture 14 of the ring member 12. The ring member 12 and the aperture 14 can be shaped so as to receive transducer probes 22 of various shapes and sizes. Accordingly, multiple block members 18 with dimensions corresponding to the different transducer probes 22 may also need to be fabricated. In operation, the transducer or ultrasound probe 22 can be introduced into the ring member 12 before the scanning process commences. The ring member 12 can subsequently be pulled back away from the patient's skin so as not to interfere with the physical contact required of the transducer probe 22 in carrying out ultrasound screening on the patient.

Figure 4:
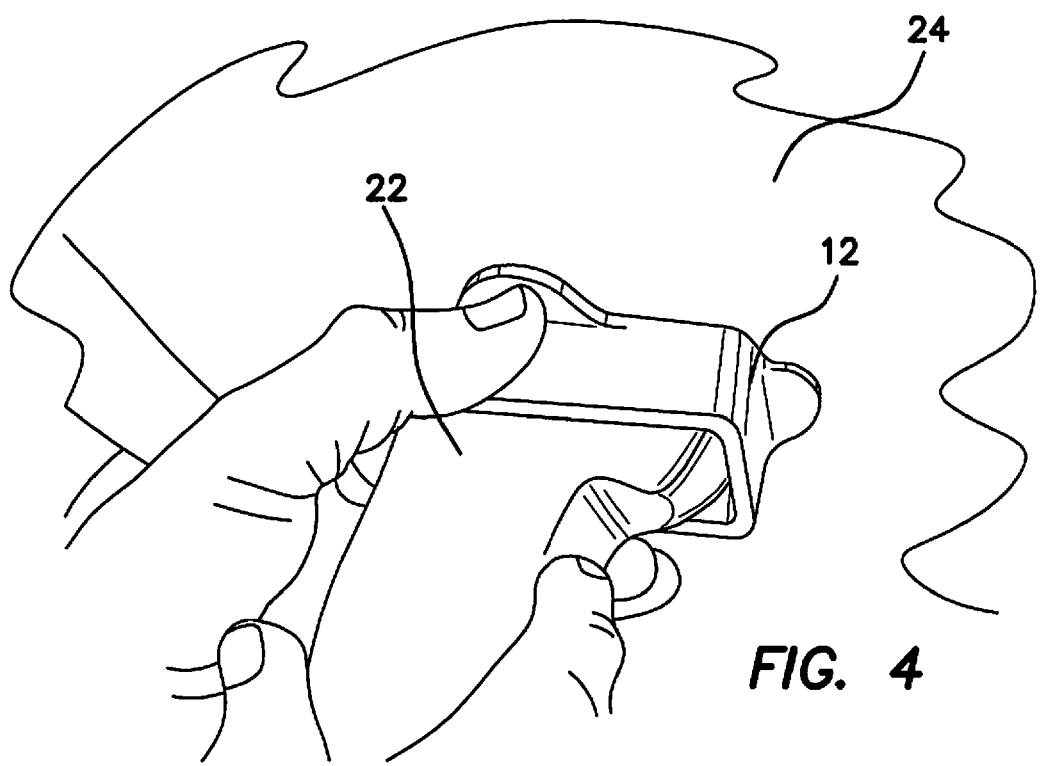
FIGS. 4-6 illustrate the device in one exemplary operation for centering the transducer probe for ultrasound scanning or other imaging purposes.
Figure 5:
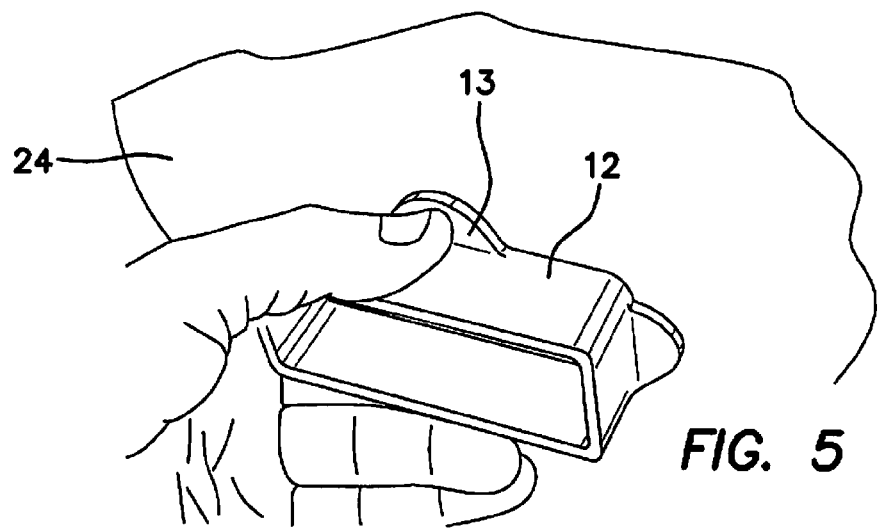
Figure 6:
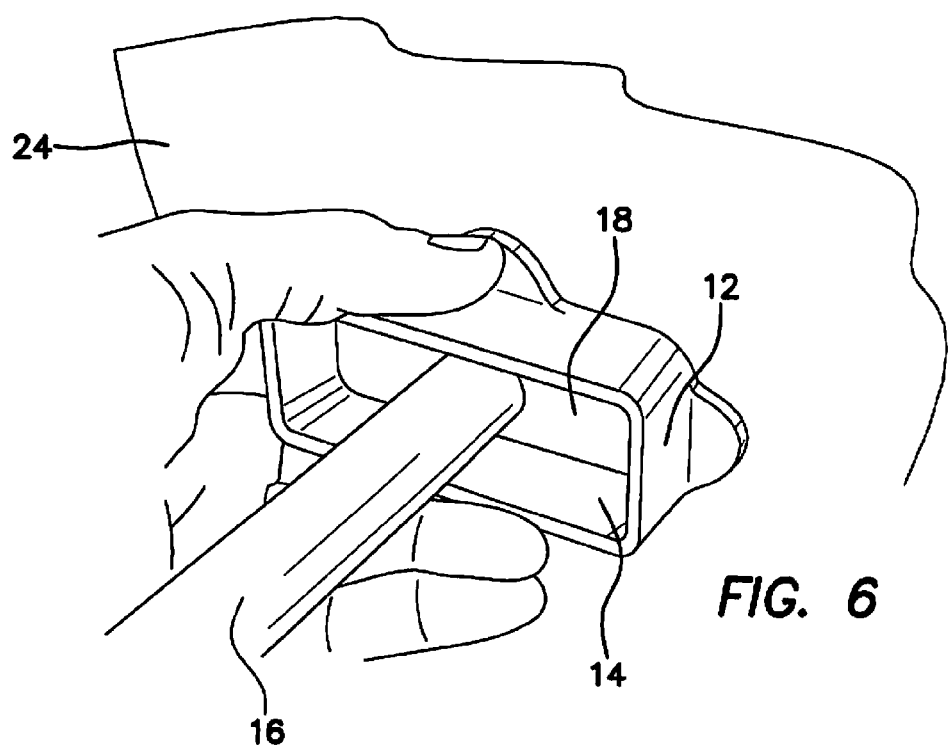

Reference is now made to FIGS. 4-6 illustrating the device 10 in operation for centering a transducer probe 22 for ultrasound and other imaging purposes. Initially, the transducer probe 22 is inserted at least partially through the ring member 12 so that the working portion of the transducer probe 22 is free to contact a patient's skin. In this configuration, as shown in FIG. 4, a first hand controls the transducer probe 22 and a second hand controls or handles the ring member 12 while the scanning procedure is completed. Once a desired area, location or site is found, as shown in FIG. 5, the transducer probe 22 is removed from the ring member 12 and the ring member 12 is pressed against the patient's skin with one hand. The ring member 14 can be handled via the grips 13.

In one embodiment, the ring member 12 may include recesses, grooves or other means for coupling the ring member 12 and transducer probe 22 such that the probe 22 can be received by and retained by the ring member 12. In one embodiment, the ring member 12 and the transducer probe 22 are configured together and can move simultaneously so that the ring member 12 does not interfere with the scanning process. In other words, the transducer probe 22 can be pressed up against the patient's skin 24 and moved about as necessary for performing the ultrasound with the ring member 12 attached thereto. In other embodiments, the transducer 22 may be snugly received within the ring member 12 such that the ring member 12 helps to stabilize the transducer probe 22 during the scanning process.

After the desired area, location or site is found, as shown in FIG. 5, the block member 18 is inserted into the aperture 14 of the ring member 12 as shown in FIG. 6. The marking protrusion 20 (not visible) is gently pressed into contact with the patient's skin 24 by pushing the handle 16 thereby making the desired indentation. Once the indentation has been made, the ring member 12 and marking member 15 are removed from the area. The indentation left behind on the skin 24 is indicative of a center position of the transducer probe 22 corresponding to the desired ultrasound view, site or location. The indentation in the skin 24 allows ultrasound scanning to be repeated with pinpoint accuracy by allowing a user to quickly find the indentation. In one embodiment, the indentation marks an injection location (e.g., epidural). The life of the indentation is based on the depth of the indentation and the nature of the patient's skin 24. In some patients the block member 18 may need to be pressed harder than with others.

Although the invention has been described in detail with reference to several embodiments, additional variations and modifications exist within the scope and spirit of the invention as described and defined in the following claims.

What is claimed is:

1. A device comprising:
    a block member having a handle, said block member including means capable of making an indentation on skin of a subject, said means capable of making an indentation on the skin of a subject being a protrusion centrally located on said block member and also configured to dispense a marking agent; and
    a ring member defining an aperture, said aperture configured to guide said block member into contact with skin of a subject, said aperture further configured to receive a transducer probe, said block member and ring member being separate and independent of one another.

2. The device of claim 1, wherein said means capable of making an indentation on skin of a subject is a circular protrusion having a dull point.

3. The device of claim 1, wherein said ring member includes one or more grips extending therefrom.

4. A device comprising:
    a block member having an elongated handle extending away from a central portion of said block member, said block member including a centrally located protrusion extending from one surface thereof, said protrusion operable to make an indentation on skin of a subject and is configured to dispense a marking agent; and
    a ring member defining an aperture, said aperture configured to guide said block member into contact with skin of a subject, said aperture is further configured to receive a transducer probe, said block member and ring member being separate and independent of one another.

5. The device of claim 4, wherein said protrusion has a circular cross-section and a dull point.

6. The device of claim 4, wherein said ring member includes one or more grips extending therefrom.

7. A method of marking a desired area on skin of a patient comprising:
    inserting a transducer probe into an aperture defined by a ring member such that said transducer probe is able to contact skin of a patient;
    pressing said transducer probe into contact with skin of a patient to locate a desired area on the patient;
    upon locating said desired area, pressing said ring member into contact with the skin of the patient near the desired area;
    removing said transducer probe from said ring member while retaining said ring member in contact with skin of a patient near said desired area; and
    inserting a marking member into said aperture defined by said ring member such that a marking protrusion on a block member of said marking member contacts skin of a patient and creates an indentation corresponding to said desired area.

8. The method of claim 7 further comprising activating an ink dispensing unit to further mark said identified area.

9. The method of claim 7 further comprising utilizing one or more grips on said ring member to control said ring member.

10. A method of marking an injection site on skin of a patient comprising:
    inserting a transducer probe into an aperture defined by a ring member such that said transducer probe is able to contact skin of a patient during use in conjunction with said ring member;
    pressing said transducer probe into contact with skin of a patient to locate a desired injection site;
    upon locating said injection site, pressing said ring member into contact with the skin of the patient near the desired injection site;
    removing said transducer probe from said ring member while retaining said ring member in contact with skin of a patient near said desired injection site; and
    inserting a marking member into said aperture defined by said ring member such that a marking protrusion on a block member of said marking member contacts skin of a patient and creates an indentation corresponding to said desired injection site.

11. The method of claim 10 further comprising activating an ink dispensing unit to further mark said identified area.

12. The method of claim 10 further comprising utilizing one or more grips on said ring member to control said ring member.

13. The method of claim 10 further comprising injecting a patient at the specific injection location.

14. A method of marking a desired area on skin of a patient comprising:

pressing a transducer probe into contact with skin of a patient to locate a desired area on the patient;

upon locating said desired area, pressing a ring member connected to said transducer probe into contact with the skin of the patient near the desired area;

removing said transducer probe from connection with said ring member while retaining said ring member in contact with skin of a patient near said desired area; and inserting a marking member into said aperture defined by said ring member such that a marking protrusion on a block member of said marking member contacts skin of a patient and creates an indentation corresponding to said desired area.

* * * * *